United States Patent
Villa et al.

[11] Patent Number: 5,916,586
[45] Date of Patent: Jun. 29, 1999

[54] PERSONAL CLEANSING SYSTEM COMPRISING POLYMERIC DIAMOND-MESH BATH SPONGE AND LIQUID CLEANSER WITH DEODORANT COMPOSITION

[75] Inventors: Virgilio Villa, Bergenfield; May Shana'a, Fort Lee; Richard Kolodziej, Cliffside Park, all of N.J.

[73] Assignee: Lever Brothers Company, Inc., New York, N.Y.

[21] Appl. No.: 08/683,554

[22] Filed: Jul. 16, 1996

Related U.S. Application Data

[60] Provisional application No. 60/002,731, Aug. 24, 1995.

[51] Int. Cl.$^6$ .................................................. A61K 7/50
[52] U.S. Cl. ...................... 424/443; 510/120; 510/153; 424/401
[58] Field of Search ........................... 424/443; 510/120, 510/133, 144, 153

[56] References Cited

U.S. PATENT DOCUMENTS

| | | |
|---|---|---|
| 1,682,119 | 8/1928 | Field . |
| 2,607,940 | 8/1952 | Miller . |
| 2,958,885 | 11/1960 | Donney . |
| 3,167,805 | 2/1965 | Zuppinger et al. . |
| 3,175,331 | 3/1965 | Klein . |
| 3,206,152 | 9/1965 | Wimmer . |
| 4,190,550 | 2/1980 | Campbell . |
| 4,228,834 | 10/1980 | Desnick . |
| 4,343,783 | 8/1982 | Hooper et al. ......................... 424/443 |
| 4,462,135 | 7/1984 | Sanford . |
| 4,480,939 | 11/1984 | Upton . |
| 4,559,157 | 12/1985 | Smith et al. .......................... 424/443 |
| 4,821,360 | 4/1989 | Giallourakis . |
| 4,917,134 | 4/1990 | Simonzi . |
| 5,007,531 | 4/1991 | Lighten . |
| 5,022,517 | 6/1991 | Benitez . |
| 5,031,759 | 7/1991 | Ogilvie . |
| 5,063,062 | 11/1991 | Greenspan et al. .................... 424/443 |
| 5,144,744 | 9/1992 | Campagnoli . |
| 5,295,280 | 3/1994 | Hudson et al. . |
| 5,366,125 | 11/1994 | Procido . |
| 5,412,830 | 5/1995 | Girardot et al. . |
| 5,462,378 | 10/1995 | Webb . |
| 5,491,864 | 2/1996 | Tuthill et al. . |

FOREIGN PATENT DOCUMENTS

| | | |
|---|---|---|
| 42864 | 1/1966 | Germany . |
| 95/00116 | 1/1995 | WIPO . |

*Primary Examiner*—Peter F. Kulkosky
*Attorney, Agent, or Firm*—Ronald A. Koatz

[57] ABSTRACT

In one embodiment the present invention relates to a personal bath or shower gel system comprising (A) a light weight polymeric meshed sponge and (B) a liquid cleanser comprising (1) an effective amount of surfactants(s) and (2) a deodorant perfume. In a second embodiment, the invention relates to a method for enhancing delivery/dispersion of deodorant perfume on skin or substrate by either applying liquid to sponge and applying sponge to substrate and/or applying liquid to skin/substrate and then rubbing skin/substrate with said sponge.

3 Claims, 1 Drawing Sheet

PERSONAL CLEANSING SYSTEM COMPRISING POLYMERIC DIAMOND-MESH BATH SPONGE AND LIQUID CLEANSER WITH DEODORANT COMPOSITION

This application is a continuation of Provision application Ser. No. 60/002,731 filed Aug. 24, 1995.

FIELD OF THE INVENTION

The present invention relates to a kit or cleansing system comprising a personal cleaning hand held bath sponge; and a liquid cleanser for bath or shower, comprising a specified deodorant composition. The invention further comprises a method for enhancing deposition of said deodorant composition in liquid cleanser compositions using a diamond-mesh bath sponge.

BACKGROUND OF THE INVENTION

The use of a sponge or system instrument to apply soap liquid cleansing compositions to the body is well known. U.S. Pat. No. 5,295,280 to Hudson et al., for example, teach a washing device for scrubbing the body. The washing member (i.e., sponge) has a substantial uniform cross-section and a substantially porous inner structure which is said to allow water and soap to permeate the surface and interior thereof (column 2, lines 28–31) U.S. Pat. No. 5,144,744 to Campagnoli also teaches sponges (specifically diamond-mesh polyethylene sponge) clearly designed for bath usage (see claim 1).

WO 95/00116 (assigned to Procter & Gamble) relates to a personal cleansing system comprising a diamond-mesh bath sponge used in combination with a liquid cleanser comprising a moisturizer. The diamond-mesh sponge is said to enhance lather profile of a cleanser containing such moisturizer. There is no mention in the World Patent of a deodorant perfume composition (known as deo perfume) and no recognition that the sponge may lead to enhanced deposition of deo perfumes.

SUMMARY OF THE INVENTION

Applicants have now unexpectedly found that deo perfumes can be readily applied and dispersed using a diamond-mesh bath sponge such as that disclosed, for example, in U.S. Pat. No. 5,144,744 to Campagnoli.

Specifically, the present invention comprises a system or kit comprising:

(1) a light weight polymeric meshed personal cleansing hand held sponge; and
(2) a liquid cleanser comprising:
  (a) an effective amount of surfactant selected from the group consisting of soap, synthetic surfactants and mixtures thereof; and
  (b) 0.01% to 10% preferably 0.05% to 5.0% of a deodorant perfume composition.

In a second embodiment, the invention comprises a method for enhancing deposition of deodorant perfume in a liquid composition comprising an effective amount of surfactant which method comprises applying said deo perfume containing cleanser to the sponge and/or desired surface (i.e., body) and applying the sponge (with or without deo perfume depending on whether cleanser was added to sponge or to body) to the desired surface. That is, the cleanser can be applied to the sponge and then applied to the body with the sponge; or the cleanser can be applied to the body and then rubbed on the body with the sponge.

DETAILED DESCRIPTION

Figure 1:
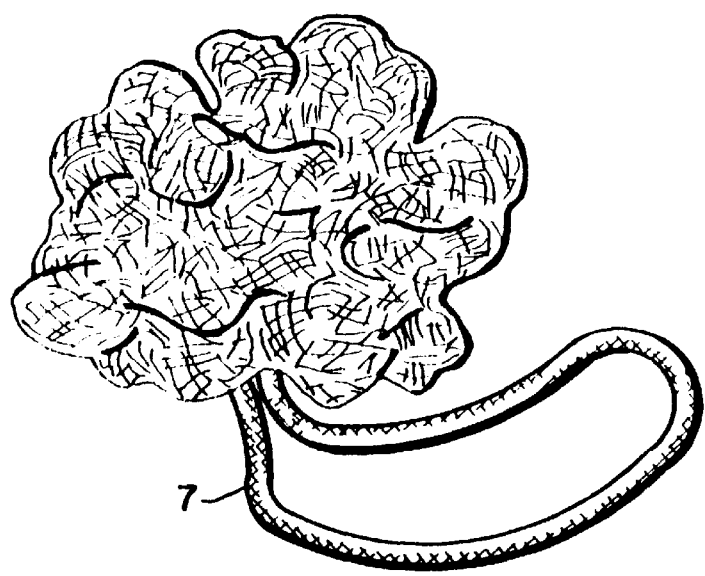
FIG. 1 is a perspective representation of a diamond mesh polymeric sponge.

The present invention is directed to the discovery that when certain deo perfume containing liquid cleansers are applied to the body/skin using a light weight polymeric meshed hand held sponge, there is greater deposition/delivery of these deo perfumes then if they had been delivered by a regular sponge. That is, the sponge synergistically interacts with the liquid cleanser plus deo perfume to enhance delivery of the deo perfume composition. The liquid cleanser containing bacteriostat and the mesh sponge are packaged together as a kit. The liquid cleanser is usually in a separate container in an amount large enough for several uses with the sponge.

More specifically, the personal bath or shower body cleansing system comprises:

(A) a light weight polymeric meshed personal cleansing hand held sponge; said polymeric mesh sponge being in a form suitable for use as a hand held cleansing implement, said hand held sponge having a diameter of from about two (2) inches to about eight (8) inches (5.08 cm. to about 20.32 cm.); preferably the polymeric meshed personal cleansing hand held polymeric mesh sponge is made of polyethylene diamond mesh and has a diameter of from 3 to 5 inches (7.62 cm. to about 12.7 cm.); and (B) a liquid cleanser comprising:
  (1) an effective amount of a surfactant selected form the group of synthetic surfactants and mixtures thereof; and
  (2) a deodorant perfume composition as described below.

The combination of polymeric mesh sponge and cleanser plus bacteriostat enhance the deposition of the bacteriostat. That is the sponge interacts with the bacteriostat to enhance delivery/deposition in a manner superior to other types of sponges.

Sponge

The cleansing polymeric mesh sponge can be prepared from readily available raw materials or with specially designed mesh materials. The polymeric mesh sponge is preferably prepared from extruded tubular netting mesh which has been prepared from special strong and flexible polymeric material. Extruded tubular netting mesh of this type, and particularly those prepared from polyethylene, have been used for the covering of meat and poultry and are readily available in industry.

The polymeric mesh sponge comprises a plurality of plys of an extruded tubular netting mesh prepared from a strong flexible polymer, preferably of the group consisting of addition polymers of olefin monomers, and polyamides of polycarboxylic acids and polyamines, said plys of tubular netting mesh are folded upon itself numerous times to form a soft ball-like polymeric mesh sponge.

The tubes or stripes of netted mesh polymer can be securely attached by means of a nylon band or suitable closure. This type of polymeric mesh sponge is disclosed in U.S. Pat. No. 4,462,135, Jul. 31, 1984, to Sanford, incorporated herein by reference.

An example of a hand-held ball-like polymeric mesh sponge is disclosed in U.S. Pat. No. 5,144,744, to Campagnoli, Sep. 8, 1992, incorporated herein by reference. It is a diamond-mesh polyethylene sponge obtained from a number of netting tubes stretched over supports, joined and bound together at the center and then released from the supports.

Commercially available "polymeric mesh sponges" are sold by The Body Shop and Bynum Concepts, Inc. Other suppliers include Supremia Use in New Jersey, Sponge Factory Dominicana in the Dominican Republic, and Integrated Marketing Group in Harrison, N.Y.

The following are some although certainly not all, specifications for suitable bath polyethylene polymeric mesh sponges:

| Size Dia. | Tubes | Ea. Length | Total Length | Wt. gm. |
|---|---|---|---|---|
| 3" | 2 | 60 cm | 120 cm | 15 |
| 4" | 4 | 50 cm | 200 cm | 23 |
| 5" | 4 | 80 cm | 320 cm | 37 |

One (1") inch = 2.54 cm; 3" = 3 × 2.54 - cm: 4" = 4 × 2.54 = cm: etc.

Figure 2:
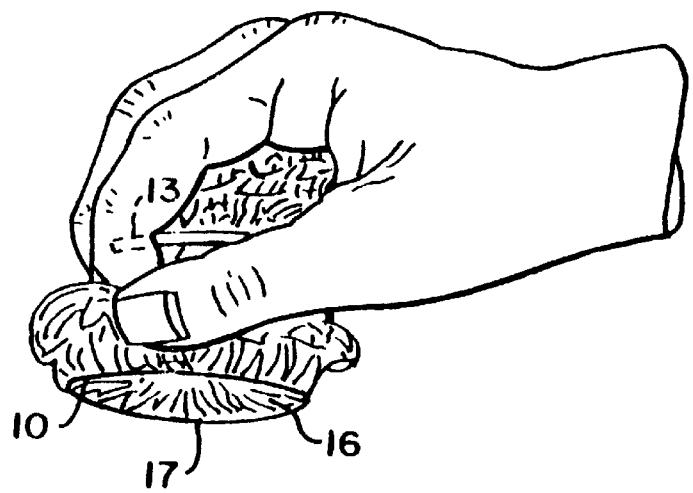
FIG. 2 is a picture showing how the sponge can be held in the hand.
Figure 3:
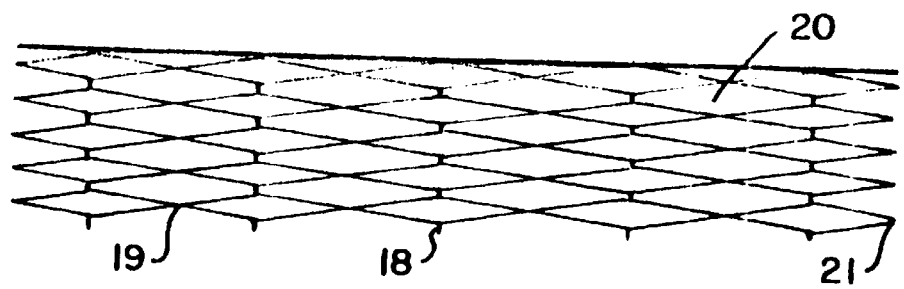
FIG. 3 shows netting mesh which can be used to make the sponge.

FIG. 1 is a perspective representation of a diamond-mesh polymeric hand held ball-like bath sponge showing a rope handle 7 which can be used in the present invention. The ease with which a cleansing polymeric mesh sponge can be held in the hand for cleaning is shown in FIG. 2. A security band 13 hold the multi-layered netting mesh together to form the polymeric mesh sponge. The netting mesh that can be used in making the polymeric mesh sponge is illustrated in FIG. 3 wherein 21 represents the mesh in stretched position. The fine polymeric filaments used in making the netting are represented by 18 with 19 representing the spot bonding of the filaments to form the open mesh 20.

Two 2 netting tubes at 60 cm length each can be used to make a 3-inch ball sponge. They can be bundled manually with a loop or rope to form a ball-like polymeric mesh sponge. Other designs such and rectangular gloves and washing implements made with the mesh material also work very well in the system of the present invention.

Liquid Cleanser—Surfactant System

The present invention relates to liquid skin cleansing compositions comprising 1 to 99% by weight, preferably 2 to 85%, more preferably 3 to 40% of a mild surfactant system comprising one or more surfactants which alone or together have been clinically tested to be milder than soap itself as measured by zein solubilization test (soap yields 80% zein solubilized). Preferably, the mildness is such that zein solubilization is in the range 10–60%. At least 10%, preferably at least 25% of the surfactant composition must be anionic surfactant. In theory, as long as the anionic is milder than soap itself, 100% of the surfactant composition may be anionic.

A number of anionic, nonionic, cationic and zwitterionic and/or amphoteric surfactants may be employed in the surfactant system of the invention provided of course that the surfactant, if used alone, or surfactant mixture is milder than would be soap itself as measured by the zein solubilization test.

Among suitable anionic co-actives are the alkyl ether sulfates, acyl isethionates, alkyl ether sulfonates, sarcosinates, sulfosuccinates, taurates and combinations thereof. Among suitable amphoteric co-actives may be included alkylbetaines, amidopropyl betaines, amidopropyl sultaines and combinations thereof.

Alkyl ether sulfates of the present invention will be of the general formula R—$(OCH_2CH_2)_n OSO_3$—$M^+$ wherein R ranges from $C_8$–$C_{20}$ alkyl, preferably $C_{12}$–$C_{15}$ alkyl, n is an integer from 1 to 40, preferably from 2 to 9, optimally about 3, and $M^+$ is a sodium, potassium, ammonium or triethanolammonium cation.

Typical commercial co-actives of this variety are listed in the Table below:

| Trademark | Chemical Name | Physical Form | Manufacturer |
|---|---|---|---|
| Steol CS 330 | Sodium Laureth Sulfate | Liquid | Stepan |
| Standopol ES-3 | Sodium Laureth Sulfate | Liquid | Henkel |
| Alkasurf ES-60 | Sodium Laureth Sulfate | Paste | Alkaril |
| Cycloryl TD | TEA Laureth Sulfate | Paste | Cyclo |
| Standopol 125-E | Sodium Laureth-12 Sulfate | Liquid | Henkel |
| Cedepal TD407MF | Sodium Trideceth Sulfate | Paste | Miranol |
| Standopol EA-2 | Ammonium Laureth Sulfate | Liquid | Henkel |

Alkyl ether sulfonates may also be employed for the present invention. Illustrative of this category is a commercial product known as Avenel S-150 commonly known as a sodium $C_{12}$–$C_{15}$ Pareth-15 sulfonate.

Another co-active type suitable for use in the present invention is that of the sulfosuccinates. This category is best represented by the monoalkyl sulfosuccinates having the formula $R_2OCCH_2CH(SO_3$—$Na^+)COO$—$M^+$; and amido-MEA sulfosuccinates of the formula: $RCONHCH_2CH_2O_2CCH_2CH(SO_3$—$M^+)COO$—$M^+$; wherein R ranges from $C_8$–$C_{20}$ alkyl, preferably $C_{12}$–$C_{15}$ alkyl and $M^+$ is a sodium, potassium, ammonium or triethanolammonium cation. Typical commercial products representative of these co-actives are those listed in the Table below:

| Trademark | Chemical Name | Physical Form | Manufacturer |
|---|---|---|---|
| Emcol 4400-1 | Disodium Lauryl Sulfosuccinate | Solid | Witco |
| Witco C5690 | Disodium Cocoamido MEA Sulfosuccinate | Liquid | Witco |
| McIntyre Mackanate CM40F | Disodium Cocoamido MEA Sulfosuccinate | Liquid | McIntyre |
| Schercopol CMSNa | Disodium Cocoamido MEA Sulfosuccinate | Liquid | Scher |
| Emcol 4100M | Disodium Myristamido MEA Sulfosuccinate | Paste | Witco |
| Schercopol | Disodium Oleamido MEA | Liquid | Scher |
| Varsulf S13333 | Disodium Ricionoleamido MEA Sulfosuccinate | Solid | Scherex |

Sarcosinates may also be useful in the present invention as a co-active. This category is indicated by the general formula $RCON(CH_3)CH_2CO_2$—$M^+$, wherein R ranges from $C_8$–$C_{20}$ alkyl, preferably $C_{12}$–$C_{15}$ alkyl and $M^+$ is a sodium, potassium ammonium or triethanolammonium cation. Typical commercial products representative of these co-actives are those listed in the Table below:

| Trademark | Chemical Name | Physical Form | Manufacturer |
|---|---|---|---|
| Hamposyl L-95 | Sodium Lauroyl Sarcosinate | Solid | W.R.Grace |
| Hamposyl TOC-30 | TEA Cocoyl/Sarcosinate | Liquid | W.R.Grace |

Taurates may also be employed in the present invention as co-actives. These materials are generally identified by the formula $RCONR'CH_2CH_2SO_3$—$M^+$, wherein R ranges from $C_8$–$C_{20}$ alkyl, preferably $C_{12}$–$C_{15}$ alkyl, R' ranges from $C_1$–$C_4$ alkyl, and $M^+$ is a sodium, potassium, ammonium or triethanolammonium cation. Typical commercial products representative of these co-actives are those listed in the Table below:

| Trademark | Chemical Name | Physical Form | Manufacturer |
|---|---|---|---|
| Igepon TC 42 | Sodium Methyl Cocoyl Taurate | Paste | GAF |
| Igepon T-77 | Sodium Methyl Oleoyl Taurate | Paste | GAF |

Within the category of amphoterics there are three general categories suitable for the present invention. These include alkylbetaines of the formula $RN^+(CH_3)_2CH_2CO_2$—$M^+$, amidopropyl betaines of the formula $RCONHCH_2CH_2CH_2N^+(CH_3)_2CH_2CO_2$—$M^+$, and amidopropyl sultaines of the formula $RCONHCH_2CH_2N^+(CH_3)_2CH_2SO_3$—$M^+$ wherein R ranges from $C_8$–$C_{20}$ alkyl, preferably $C_{12}$–$C_{15}$, alkyl, and $M^+$ is a sodium, potassium, ammonium or triethanolammonium cation. Typical commercial products representative of these co-actives are found in the Table below:

| Trademark | Chemical Name | Physical Form | Manufacturer |
|---|---|---|---|
| Tegobetaine F | Cocamidopropyl Betaine | Liquid | Goldschmidt |
| Lonzaine C | Cocamidopropyl Betaine | Liquid | Lonza |
| Lonzaine CS | Cocamidopropyl Hydroxysultaine | Liquid | Lonza |
| Lonzaine 12C | Coco-Betaine | Liquid | Lonza |
| Schercotaine MAB | Myristamidopropyl Betaine | Liquid | Lonza |
| Velvetex OLB-50 | Oleyl Betaine | Paste | Henkel |

Within the broad category of liquid actives, the most effective are the alkyl sulfates, alkyl ether sulfates, alkyl ether sulfonates, sulfosuccinates, and amidopropyl betaines.

Another preferred surfactant is an acyl isethionate having the formula

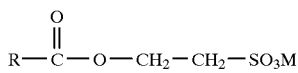

in which R denotes a linear or branched alkyl group and M denotes an alkali metal or alkaline earth metal or an amine.

Another surfactant which may be used are the monoalkyl or dialkylphosphate surfactants.

Another mild surfactant which may be used, preferably used as primary surfactant in combination with other surfactants noted above, is sodium coco glyceryl ether sulfonate. While desirable to use because of its mildness properties, this coco AGS alone does not provide optimum lather creaminess. A sodium 90/10 coconut/tallow alkyl AGS distribution is preferred for creaminess. Salts other than the sodium salt such as TEA-, ammonium, and K-AGS and chain length distributions other than 90/10 coconut/tallow are usable at moderate levels. Also, some soap may be added to improve lather volume and speed of lathering. Certain secondary co-surfactants used in combination with AGS can also provide a creamier and more stable lather. These secondary surfactants should also be intrinsically mild. One secondary surfactant that has been found to be especially desirable is sodium lauroyl sarcosinate (trade name Hamposyl L, made by Hampshire Chemical).

The amphoteric betaines and sultaines noted above can be used as the sole surfactant, but are more preferred as a co-surfactant. Nonionics generally should not be used as the sole surfactant in this product if high foaming is desirable; however, they can be incorporated as a co-surfactant.

Nonionic and cationic surfactants which may be used include any one of those described in U.S. Pat. No. 3,761,418 to Parran, Jr., hereby incorporated by reference into the subject application. Also included are the aldobionamides as taught in U.S. Pat. No. 5,389,279 to Au et al; and the polyhydroxy fatty acid amides as taught in U.S. Pat. No. 5,312,934 to Letton, both of which are incorporated by reference into the subject application.

Soaps can be used at levels of about 1 to 10%. Soaps can be used at higher level provided that the surfactant mixture is milder than soap. The soaps may be added neat or made in situ via adding a base, e.g., NaOH; to convert free fatty acids.

Of course, as noted above, soaps should only be used as cosurfactants to the extent that the surfactant system is milder than soap alone.

A preferred surfactant active system is one such that acyl isethionate comprises 1 to 15% by weight of the total composition, an anionic other than acyl isethionate (e.g., ammonium lauryl ether sulfate) comprises 1 to 15% by weight of the total composition and amphoteric comprises 0.5 to 15% by weight of the total composition.

Another preferred active system is one comprising 1 to 20% alkyl ether sulfate. Preferred surfactant active systems may also contain 1 to 10% alkali metal lauryl sulfate or $C_{14}$–$C_{16}$ olefin sulfonate instead of acyl isethionate.

Another preferred cleansing and moisturizing cleansing composition can contain ingredients selected from the group consisting of:

(a) 8% to 35% polyol;

(b) 35% to 70%, preferably 40% to 65% water;

(c) 5% to 20%, preferably 7% to 19%, of mostly insoluble saturated (low iodine value of zero to 15) $C_8$–$C_{22}$ fatty acid potassium soap;

(d) 0.1% to 7%, preferably 0.5 to 5%, of free $C_8$–$C_{22}$ fatty acids; and (e) 0.5% to 5%, preferably 0.7% to about 4.5% petrolatum, and mixtures thereof.

The polyol is selected from the group consisting of: glycerin, glycerol, propylene glycol, polypropylene glycols, polyethylene glycols, ethyl hexanediol, hexylene glycols, and other aliphatic alcohols; and mixtures thereof. When propylene glycol is used as a moisturizer, it is used at a level of at least 5%. The polyols are preferably used at levels of from about 10–30%.

The liquid cleanser can contain from about 0.5% to about 15% of a lipophilic emollient moisturizer selected from the group consisting of: petrolatum; esters of fatty acids; glycerin mono-, di-, and tri-esters; epidermal and sebaceous hydrocarbons such as cholesterol, cholesterol esters, squalene, squalene; silicone oils and gums; mineral oil; lanolin and derivatives and the like; and mixtures thereof.

A preferred improved stable product with a moisturizing benefit is achieved with the incorporation of larger sized petrolatum particles into selected fatty acid/soap matrixes. The larger sized petrolatum particles will vary for a liquid or semi-solid. The key is to select the fatty acid and/or soap matrix and to mix in the petrolatum using a minimal controlled amount of shear to maintain larger petrolatum particles and achieve a homogeneous stable product, e.g., an improved benefit is also achieved in a semi-solid cleansing cream.

Any fatty acid matter (free and neutralized) used in the liquid cleanser preferably has an Iodine Value (I.V.) of from zero to about 15, preferably below 10, more preferably below 3.

The Deodorant Composition

The characterizations of the deodorant composition of the invention presents difficulties, since it cannot be defined solely in terms of substances of specified structure and combinations in specified proportions. Nevertheless, procedures have been discovered that enable the essential materials of the deodorant compositions to be identified by tests.

The essential materials required for the formulation of deodorant compositions are those having a lipoxidase-inhibiting capacity of at least 50% or those having a Raoult variance ratio of at lest 1.1, as determined by the following tests, which are designated the lipoxidase and morpholine tests respectively.

The Lipoxidase Test

In this test the capacity of a material to inhibit the oxidation of linoleic acid by lipoxidase (ECI.13.1.13) to form a hydroperoxide is measured.

Aqueous 0.2 M sodium borate solution (pH 9.0) is used as buffer solution.

A control substrate solution is prepared by dissolving linoleic acid (2.0 ml) in absolute ethanol (60 ml), diluting with distilled water to 100 ml and then adding borate buffer (100 ml) and absolute ethanol (300 ml).

A test substrate solution is prepared in the same way as the control substrate solution except that for the absolute ethanol (300 ml) is substituted the same volume of a 0.5% by weight solution in ethanol of the material to be tested.

A solution of the enzyme lipoxidase in the borate buffer and having an activity within the range of from 15,000 to 40,000 units per ml is prepared.

The activity of the lipoxidase in catalyzing the oxidation of linoleic acid is first assayed spectrophotometrically using the control. An automatic continuously recording spectrophotometer is used and the increase in extinction at 234 nm (the peak of hydroperoxide) is measured to follow the course of oxidation, the enzyme concentration used being such that it gives an increase in optical density ($\Delta$OD) at 234 nm within the range of from 0.6 to 1.0 units per minute. The following ingredients are placed in two 3 ml cuvettes:

|  | Control (ml) | Blank (ml) |
| --- | --- | --- |
| Control substrate solution | 0.10 | 0.10 |
| Absolute ethanol | 0.10 | 0.10 |
| Borate buffer | 2.75 | 2.80 |
| Lipoxidase solution | 0.05 | — |

The lipoxidase solution is added to the control cuvette last and the reaction immediately followed spectrophotometrically for about 3 minutes with recording of the increase in optical density at 234 nm as a curve on a graph.

The capacity of a material to inhibit the oxidation is then measured using a test sample containing enzyme, substrate and a deodorant material. The following ingredients are placed in two 3 ml cuvettes.

|  | Test Sample (ml) | Blank (ml) |
| --- | --- | --- |
| Test substrate solution | 0.10 | 0.10 |
| Absolute ethanol | 0.10 | 0.10 |
| Borate buffer | 2.75 | 2.80 |
| Lipoxidase solution | 0.05 | — |

The lipoxidase solution is added to the test sample cuvette last and the course of the reaction immediately followed as before.

The lipoxidase-inhibiting capacity of the material is then calculated from the formula $100(S_1-S_2)/S_1$, where $S_1$ is the slope of the curve obtained with the control and $S_2$ is the slope of the curve obtained with the test sample, and thus expressed as % inhibition. A material that gives at least 50% inhibition interest is hereafter referred to as having a lipoxidase-inhibiting capacity of at least 50%.

The Morpholine Test

In this test the capacity of a material to depress the partial vapor pressure of morpholine more than that required by Raoult's Law is measured. Substances that undergo chemical reaction with morpholine, for example aldehydes, are to be regarded as excluded from the test.

Into a sample bottle of capacity 20 ml is introduced morpholine (1 g) the bottle fitted with a serum cap and then maintained at 37° C. for 30 minutes for equilibrium to be reached. The gas in the headspace of the bottle is analyzed by piercing the serum cap with a capillary needle through which nitrogen at 37° C. is passed to increase the pressure in the bottle by a standard amount and then allowing the excess pressure to inject a sample from the headspace into gas chromatograph apparatus, which analyses it and provides a chromatographic trace curve with a peak due to morpholine, the area under which is proportional to the amount of morpholine in the sample.

The procedure is repeated under exactly the same conditions using instead of morpholine alone, morpholine (0.25 g) and the material to be tested (1 g): and also using the material (1 g) without the morpholine to check whether it gives an interference with the morpholine peak (which is unusual).

The procedure is repeated until reproducible results are obtained. The areas under the morpholine peaks are measured and any necessary correction due to interference by the material is made.

A suitable apparatus for carrying out the above procedure is a Perkin-Elmer Automatic GC Multifract F40 for Head Space Analysis. Further details of this method are described by Kolb in "CZ-Chemie-Technik", Vol. 1, No. 2, 87–91 (1972) and by Jentzsch et al. in "Z. Anal. Chem." 236, 96–118 (1968).

The measured areas representing the morpholine concentration are proportional to the partial vapor pressure of the morpholine in the bottle headspace. If A is the area under the morpholine peak when only morpholine is tested and A' is the area due to morpholine when a material is present, the relative lowering of partial vapor pressure of morpholine by the material is given by 1−A'/A.

According to Raoult's Law, if at a given temperature the partial vapor pressure of morpholine in equilibrium with air above liquid morpholine is p, the partial vapor pressure p' exerted by morpholine in a homogeneous liquid mixture of morpholine and material at the same temperature is pM/(M+PC), where M and PC are the molar concentrations of morpholine and material. Hence, according to Raoult's Law the relative lowering of morpholine partial vapor pressure (p−p')/p, is given by 1−M/(M+PC), which under the circumstances of the test is 87/(87+m/4), where m is the molecular weight of the perfume material.

The extent to which the behaviors of the mixture departs from Raoult's Law is give by the ratio $$\frac{1 - A'/A}{87/(87 + m/4)}$$

The above ratio, which will be referred to as the Raoult variance ratio, is calculated from the test results. Where a material is a mixture of compounds, a calculated or experimentally determined average molecular weight is used for m. A material that depresses the partial vapor pressure of morpholine by at least 10% more than that required by Raoult's Law is one in which the Raoult variance ratio is at least 1.1.

A large number of materials which satisfy one or both tests is described later in this specification and these are hereafter referred to as "components", in contrast to other materials which fail both tests which are referred to as "ingredients".

Before defining the more detailed aspects of the invention so far as it relates to deodorant compositions, it is necessary to clarify some of the terms that will be employed.

A composition is a blend of organic compounds. For the purposes of this specification it is necessary to identify the "components" in the composition. This is done by first describing the composition in terms of four categories. These categories are given below. Examples of components in each category are provided.

(1) Single chemical compounds whether natural or synthetic, e.g., coumarin (natural or synthetic), iso-eugenol, benzyl salicylate. The majority of components are in this category.

(2) Synthetic reaction products (products of reaction), mixtures of isomers and possibly homologous, e.g., α-iso-methyl ionone.

(3) Natural oils, gums and resins, and their extracts, e.g., patchouli oil, geranium oil, clove leaf oil, benzoin resinoid.

(4) Synthetic analogues of category 3. This category includes materials that are not strict analogues of natural oils, gums and resins but are materials that result from at attempts to copy or improve upon materials of category 3, e.g., Bergomot AB 430, Geranium AB 76, Pomeransol AB 314.

Components of Categories (3) and (4) although often uncharacterized chemically are available commercially.

Where a material is supplied or used conventionally for convenience as a mixture, e.g., p-t-Amylcyclohexanone diluted with diethyl phthalate, for the purposes of this specification two components are present, so that use of 5% of a blend of 1 part of this ketone and 9 parts of diethyl phthalate is represented as 0.5% of the ketone and 4.5% of diethyl phthalate.

It has been found advantageous in formulating the most effective deodorant composition for incorporation into the detergent product of the invention to use components that, as well as satisfying the lipoxidase or morpholine tests, satisfy further conditions. These conditions are:

(i) there must be at least five components present, (ii) each of these components must be selected from at least four different chemical classes (to be defined below), (iii) a component from each of classes 1, 2 and 4 must be present, (iv) at least 45%, preferably at least 50 and most preferably from 60 to 100%, by weight of the deodorant composition must comprise components, (v) a component is not considered to contribute to the efficacy of the deodorant composition if it is present in the deodorant composition at a concentration of less than 0.5% by weight, and (vi) a class is not considered to contribute to the efficacy of the deodorant composition if it is present in the deodorant composition at a concentration of less than 0.5% by weight.

Therefore, according to a preferred embodiment of the invention, there is provided a deodorant detergent product as herein defined in which the deodorant composition consists essentially of from about 45 to 100% by weight of at least five components and from 0 to about 55% by weight of ingredients, each of the components being selected from components having a lipoxidase inhibiting capacity of at least 50% and components having a Raoult variance ratio of at least 1.1, the components and ingredients being so chosen that the deodorant value of the deodorant composition is within the range of 0.50 to 3.5.

Each component should be allocated to one of six classes. These classes are:

Class 1—Phenolic substances;

Class 2—Essential oils, extracts, resins, "synthetic" oils (denoted by "AB");

Class 3—Aldehydes and ketones;

Class 4—Polycyclic compounds;

Class 5—Esters;

Class 6—alcohols.

In attributing a component to a class, the following rules are to be observed. Where the component could be assigned to more than one class, the component is allocated to the class occurring first in the order given above: for example clove oil, which is phenolic in character, is placed in Class 1 although it otherwise might have been allocated to Class 2. Similarly, 2-n-heptyl cyclopentanone which is a polycyclic ketone is attributed to Class 3 instead of Class 4.

The following are examples of deodorant components that either have a lipoxidase inhibiting capacity (LIC) of at least 50% or have a Raoult variance ratio (RVR) of at least 1.1. Their class, molecular weight (m), LIC and RVR as determined by the tests already described herein are also listed.

The nomenclature adopted for the components listed below and for the ingredients which appear in the deodorant formulations of the Examples is, so far as is possible, that employed by Steffen Arctander in "Perfume and Flavor Chemicals (Aroma Chemicals)" Volume I and II (1969) and the "Perfume & Flavor Materials of Natural Origin" (1960) by the same author. Where a component or other ingredient is not described by Arctander, then either the chemical name is given or, where this is not known (such as is the case with perfumery house specialties), then the supplier's identity can be established by reference to the appendix which appears at the end of the specification.

|  | LIC | RVR | m |
|---|---|---|---|
| Class I - Phenolic Substances | | | |
| iso-amyl salicylate | 95 | 1.24 | 208 |
| Benzyl salicylate | 0 | 1.58 | 228 |
| Carvacrol | 32 | 1.43 | 150 |
| Clove leaf oil | 79 | 1.43 | 164 |
| Ethyl vanillin | 100 | 1.43 | 152 |
| iso-Eugenol | 100 | 1.48 | 164 |
| LRG 201 | 100 | 1.21 | 196 |
| Mousse de chene Yugo | 98 | 1.29 | 182 |
| Pimento leaf oil | 100 | — | 165 |
| Thyme oil red | 55 | 1.37 | 150 |
| Class 2 - Essential oils, extracts resins. "synthetic" oils. (denoted by "AB") | | | |
| Benzoin Siam resinoids | 87 | — | — |
| Bergamot AB 37 | 58 | 0.97 | 175 |
| Bergamot AB 430 | 58 | 0.97 | 175 |
| Geranium AB 76 | 26 | 1.29 | 154 |
| Geranium oil | 26 | 1.29 | 154 |
| Opoponax resinoid | 96 | 1.33 | 150 |
| Patchouli oil | 76 | 1.25 | 140 |
| Petitgrain oil | 34 | 1.27 | 175 |
| Pomeransol AB 314 | 100 | — | — |
| Class 3 - Aldehydes and Ketones | | | |
| 6-Acetyl-1,1,3,4,4,6-hexamethyl-tetrahydronaphthalene | 100 | 1.03 | 258 |
| p-t-Amyl cyclohexanone | 50 | 1.10 | 182 |
| p-t-Butyl-α-methyl hydrocinnamic aldehyde | 74 | — | 204 |
| 2-n-Heptylcyclopentanone | 56 | 1.05 | 182 |
| α-iso-Methyl ionone | 100 | 1.13 | 206 |
| β-Methyl naphthyl ketone | 100 | 0.96 | 170 |
| Class 4 - Polycyclic Compounds | | | |
| Coumarin | 58 | 1.22 | 146 |
| 1,3,4,6,7,8-Hexahydro-4,6,6,7,8,8-hexamethyl cyclopenta-γ-2-benzopyran | 100 | — | 240 |
| 3a-Methyl-dodecahydro-6,6,9a-trimethylnaphtho(2,1-b)furan | 58 | 1.30 | 230 |
| β-Naphthyl methyl ether | 100 | — | 158 |
| Class 5 - Esters | | | |
| o-t-Butylcyclohexyl acetate | 52 | 1.08 | 198 |
| p-t-Butylcyclohexyl acetate | 54 | 0.98 | 198 |
| Diethyl phthalate | 79 | 1.20 | 222 |
| Nonanediol-1,3-diacetate | 33 | 1.17 | 244 |
| Nonanolide-1:4 | 92 | 0.87 | 156 |
| i-Nonyl acetate | 50 | 0.83 | 186 |
| i-Nonyl formate | 19 | 1.49 | 172 |
| Class 6 - Alcohols | | | |
| Dimyrcetol | 016 | 1.22 | 156 |
| Phenylethyl alcohol | 22 | 1.24 | 122 |
| Tetrahydromuguol | 24 | 1.23 | 158 |

It has been shown that for best results, a certain minimum average concentration of components should be present. This minimum concentration is a function of the number of classes present the more classes present, the lower the minimum concentration. The minimum average concentration in the various situations that can apply is shown in the Table below:

| Number of classes represented in deodorant composition | Average concentration of components | |
|---|---|---|
| | minimum not less than (%) | preferably not less than (%) |
| 4 | 5 | 6 |
| 5 | 4.5 | 5.5 |
| 6 | 4.5 | 5 |

Also, it is preferred that at least 1% of each of four classes is present in the deodorant composition, but individual components which are present at a concentration of less than 0.5% are eliminated from this calculation, as is the class into which they fall if there is present no component at a concentration of at least 0.5% which falls within that class.

More specifically, the invention also provides a deodorant detergent product as herein defined wherein the amount of deodorant components in the deodorant composition present in the classes 1, 2 and 4 as herein defined is at least 1%, most preferably at least 3% by weight of the deodorant composition for each class, and the amount of components present in each of at least two other classes is at least 1% by weight of the composition, provided also that any component that is present in the deodorant composition at a concentration of less than a threshold value of 0.5% by weight is eliminated from the calculation of the amounts of components in each class.

Although at least four different classes of components should preferably be represented in the deodorant composition, superior compositions can be obtained if more than four classes are represented. Accordingly, five or six classes can be represented in the deodorant composition.

It has been shown by the preparation, examination and testing of many hundreds of deodorant compositions that the best results are obtained by keeping within the aforementioned rules when selecting types and amounts of components and ingredients. For example, deodorant compositions which contain less than the minimum concentration of components of 45% are unlikely to result in a deodorant composition having a deodorant value of at least 0.50. Therefore, in preparing the best deodorant compositions of the invention, the rules for selection of components according to their classification, the representation of different classes, the amounts of each component present, bearing in mind the threshold value below which it is believed a component will not significantly contribute, are all important to observe if the best results are to be obtained.

It should be explained that components present in the deodorant detergent product for purposes other than obtaining deodorant effects, for example an adjunct like the anti-oxidant, are excluded from the operation of the preceding instructions to the extent that the component is required for that other purpose. The levels at which adjuncts are conventionally present in detergent products is well established for established materials and readily determinable for new materials so that the application of the above exclusion presents no difficulty.

Deodorant compositions can be incorporated in deodorant detergent products according to the invention, at a concentration of from about 0.01 to about 10%, preferably from 0.5 to 5% and most preferably from 1 to 3% by weight.

It is apparent that if less than 0.01% of a deodorant composition is employed, then use of the detergent product is unlikely to provide a significant reduction in body malodor intensity. If more than 10% of a deodorant composition is employed, then use of the detergent product is unlikely to further reduce body malodor intensity beyond that observed at the 10% level.

The present invention is directed to the unexpected observation that these deodorant compositions, when applied with the mesh sponge described above, were much better dispersed/deposited than if applied with other types of sponges.

Other Ingredients

The cleansing bath/shower compositions can contain a variety of nonessential optional ingredients suitable for rendering such compositions more desirable. Such conventional optional ingredients are well known to those skilled in the art, e.g., preservatives such as benzyl alcohol, methyl paraben, propyl paraben and imidazolidinyl urea; other thickeners and viscosity modifiers such as $C_8$–$C_{18}$ ethanolamide (e.g., coconut ethanolamide); pH adjusting agents such as citric acid, succinic acid, phosphoric acid, sodium hydroxide, etc.; suspending agents such as magnesium/aluminum silicate; perfumes; dyes; and sequestering agents such as disodium ethylenediamine tetraacetate.

If present, the optional components individually generally comprise from about 0.001% to about 10% by weight of the composition, but can be more or less.

Optional thickeners are categorized as cationic, nonionic, or anionic and are selected to provide the desired viscosity. Suitable thickeners are listed in the Glossary and Chapters 3, 4, 12 and 13 of the *Handbook of Water-Soluble Gums and Resins,* Robert L. Davidson, McGraw-Hill Book Co., New York, N.Y., 1980, incorporated by reference herein.

The liquid personal cleansing products can be thickened by using polymeric additives that hydrate, swell or molecularly associate to provide body (e.g., hydroxypropyl guar gum is used as a thickening aid in shampoo compositions).

A suitable thickener is hydroxy ethyl cellulose, e.g., Natrosol R 250 KR sold by The Aqualon Company.

Another thickener is acrylated steareth-20 methylacrylate copolymer sold as Acrysol ICS-1 by Rohm and Haas Company.

The amount of polymeric thickener found useful in the present compositions is about 0.1% to about 2%, preferably from about 0.2% to about 1.0%.

The liquid cleanser can be made with from about 0.1% to about 5%, preferably from about 0.3% to about 3%, of a skin moisturizing cationic polymer selected from the group consisting of: cationic polysaccharides and derivatives, cationic copolymers of saccharides and synthetic monomers, synthetic copolymers and cationic protein derivatives.

In a second embodiment of the invention, the invention relates to a method of enhancing delivery/deposition of deo perfume which method comprises applying liquid cleanser comprising said bacteriostat to skin or to mesh sponge and rubbing or massaging said sponge over area where enhanced delivery/deposition is desired.

Specifically, the method comprises applying to a substrate selected from the group consisting of skin, a polymeric meshed sponge and combinations thereof a liquid cleanser comprising:

(1) an effective amount of surfactant selected from synthetic surfactants and mixtures thereof; and (2) deodorant perfume composition rubbing said polymeric mesh sponge against skin to spread the liquid cleanser.

EXAMPLE 1

The polymeric mesh sponge was packaged in a kit which contained a liquid cleanser comprising as follows:

| INGREDIENT | % BY WEIGHT |
| --- | --- |
| Acyl Isethionate | 1–15% |
| Anionic other than Acyl Isethionate(SLES)* | 1–15% |
| Amphoteric Surfactant** | 5–15% |

-continued

| INGREDIENT | % BY WEIGHT |
| --- | --- |
| Sequestrant (EDTA or EHDP) | 0.01–0.1% |
| Moisturizer (e.g. cationic polymer) | 0.05–3.0% |
| Standard additives (e.g., dyes, perfumes) | 0.01–10% |
| DP300 (Triclosan) | .1–1% |
| Water | Balance |

*Sodium lauryl ether sulfate
**Cocamidopropyl betaine

EXAMPLE 2

The polymeric mesh was packaged in a kit that contained a liquid cleanser comprising as follows:

| Ingredient | % by wt. |
| --- | --- |
| Acyl isethionate | 1–15 |
| Anionic other than acyl isethionate | 1–15 |
| Amphoteric | 20–30 |
| Moisturizer (e.g., silicone) | 3–7 |
| Minors (perfumes, preservatives) | 0.1–10 |
| Triclosan | 0.1–1 |
| Water | Balance |

EXAMPLE 3

The polymeric mesh sponge is packaged in a kit which contains a liquid cleanser as follows:

| Composition | Approximate % by wt. |
| --- | --- |
| Ammonium Lauryl Sulfate | 6.6 |
| Sodium Laureth Sulfate | 5.2 |
| Lauramide DEA | 3.5 |
| Glycerin | 1.5 |
| Isostearamidopropyl Morpholine Lactate | 0.6 |
| Citric Acid | 0.2 |
| Disodium Ricinoleamido MEA Sulfosuccinate | 0.1 |
| Triclosan | 0.2 |
| Water | 80.9 |
| Dyes, EDTA, Hydantoin | |

EXAMPLE 4

The polymeric mesh is packaged in a kit which contain a liquid cleanser comprising as follows:

| Composition | Estimated % by Wt. |
| --- | --- |
| Glycerin | 19.5 |
| Sodium Soap | 14.1 |
| Disodium Lauroamphodiacetate | 3.5 |
| Cocamidopropyl Betaine | 1.5 |
| Lauramide DEA | 2.0 |
| Triethanolamine | 0.9 |
| Water | 55.7 |
| BHT | Minor |
| Citric Acid | Minor |
| Methylparaben | Minor |
| Trisodium HEDTA | Minor |
| Propylparaben | Minor |
| Colorants | Minor |
| Perfume | Minor |

We claim:

1. A personal bath or shower bath cleansing system comprising:

(A) a light weight polymeric diamond meshed personal cleansing hand held sponge; said polymeric diamond mesh sponge being in a form suitable for use as a hand held cleansing implement; and (B) a liquid cleanser comprising
- (1) a surfactant system comprising:
  - (a) 1 to 15% by wt. total composition of an acyl isethionate;
  - (b) 1 to 15% by wt. total composition of an anionic surfactant other than acyl isethionate; and
  - (c) 0.5 to 15% by wt. total composition amphoteric; and
- (2) 0.01 to 10% by wt. of a deodorant composition comprising from 45 to 100% by weight of deodorant components, said components having a lipoxidase-inhibiting capacity of at least 50% or a Raoult variance ratio of at least 1.1, said components being classified into six classes consisting of:
  - Class 1: phenolic substances;
  - Class 2: essential oils, extracts, resins and synthetic oils;
  - Class 3: aldehydes and ketones;
  - Class 4: polycyclic compounds;
  - Class 5: esters;
  - Class 6: alcohols,
  provided that where a component can be classified into more than one class, it is placed in the lower or lowest numbers class:
  said components being so selected that
  - (a) the deodorant composition contains at lest five components of which at least one must be selected from each of class 1, class 2 and class 4;
  - (b) the deodorant composition contains components from at least 4 of the 6 classes; and
  - (c) any component present in the deodorant composition at a concentration of less than 0.5% by weight of said composition is eliminated from the requirements of (a) and (b) said deodorant composition having a deodorant value of from 0.50 to 3.5 as measured by Deodorant Value Test, wherein the odor intensity of said cleanser (B) is higher when used with said polymeric diamond mesh sponge than if used with other conventional sponges.

2. A system according to claim 1 wherein the light weight polymeric meshed personal cleansing hand held polymeric mesh sponge is made of polyethylene diamond mesh and has a diameter of from 3 to 5 inches (7.62 cm to about 12.7 cm).

3. A method of enhancing delivery/deposition of bacteriostat comprising:
- (a) applying to a substrate selected from the group consisting of skin, a polymeric diamond meshed sponge and combinations thereof:
  - (1) an effective amount of surfactant system comprising:
    - (a) 1 to 15% by wt. total composition of an acyl isethionate;
    - (b) 1 to 15% by wt. total composition of an anionic surfactant other than acyl isethionate; and
    - (c) 0.5 to 15% by wt. total composition amphoteric; and
  - (2) a deodorant perfume composition as defined in claim 1; and
- (b) rubbing said polymeric meshed sponge against skin to spread the liquid cleanser wherein the odor intensity of the liquid cleanser of (1)(a)(b)(c) and (2) is higher when used with said polymeric diamond mesh sponge than if used with other conventional sponges.

* * * * *